United States Patent [19]

Dosoretz et al.

[11] Patent Number: 5,770,156
[45] Date of Patent: Jun. 23, 1998

[54] GAS DETECTION AND MEASUREMENT SYSTEM

[75] Inventors: Victor J. Dosoretz, Newton Center; Daniel Behr, Needham; Scott Keller, Lincoln, all of Mass.

[73] Assignee: IN USA, Inc., Needham, Mass.

[21] Appl. No.: 658,020

[22] Filed: Jun. 4, 1996

[51] Int. Cl.$^6$ .................................................. G01N 21/59
[52] U.S. Cl. ........................... 422/91; 436/164; 356/434; 356/438
[58] Field of Search ............................ 422/82.05, 82.09, 422/91; 436/164, 165; 356/434, 435, 437

[56] References Cited

U.S. PATENT DOCUMENTS

| | | | |
|---|---|---|---|
| 3,727,050 | 4/1973 | Kerr | 250/43.5 |
| 3,761,724 | 9/1973 | Dennis | 250/565 |
| 3,843,258 | 10/1974 | Shupe | 356/88 |
| 3,916,195 | 10/1975 | Burch et al. | 250/345 |
| 3,925,667 | 12/1975 | Staab | 250/343 |
| 3,937,962 | 2/1976 | Faulhaber et al. | 250/346 |
| 3,970,387 | 7/1976 | Faulhaber et al. | 356/51 |
| 4,061,918 | 12/1977 | Preier et al. | 250/343 |
| 4,126,396 | 11/1978 | Hartmann et al. | 356/434 |
| 4,156,143 | 5/1979 | Adrian | 250/343 |
| 4,156,812 | 5/1979 | Staab | 250/345 |
| 4,180,732 | 12/1979 | Fabrinski et al. | 250/344 |
| 4,281,248 | 7/1981 | Fabinski et al. | 250/345 |
| 4,500,207 | 2/1985 | Maiden | 356/409 |
| 4,557,603 | 12/1985 | Oehler et al. | 356/418 |
| 4,560,875 | 12/1985 | Crowder | 250/343 |
| 4,567,366 | 1/1986 | Shinohara | 250/339 |
| 4,676,642 | 6/1987 | French | 356/346 |
| 4,941,747 | 7/1990 | Dakin | 356/346 |
| 5,040,895 | 8/1991 | Laurent et al. | 356/346 |
| 5,146,283 | 9/1992 | Parnoff et al. | 356/246 |
| 5,173,749 | 12/1992 | Tell et al. | 356/437 |
| 5,222,389 | 6/1993 | Wong | 73/31.02 |
| 5,298,751 | 3/1994 | Fee et al. | 250/338.5 |
| 5,396,328 | 3/1995 | Jestel et al. | 356/358 |

*Primary Examiner*—Jeffrey Snay
*Attorney, Agent, or Firm*—Weingarten, Schurgin, Gagnebin & Hayes LLP

[57] ABSTRACT

A gas detection and measurement system includes a light source, a light sensor, a test cell body having a first fluid port and a second fluid port, and first and second optical paths from the light source to the light sensor through the test cell. The first and second optical paths have different lengths. As fluid flows through the test cell body, light intensity measurements are taken along the first and second optical paths so that the concentration of a target gas within the fluid can be calculated.

15 Claims, 3 Drawing Sheets

GAS DETECTION AND MEASUREMENT SYSTEM

FIELD OF THE INVENTION

This invention relates to gas detection and measurement, and more particularly to an apparatus for measuring gas concentration of a selected gas in a fluid.

BACKGROUND OF THE INVENTION

Spectrochemical analysis includes a number of techniques for determining the presence or concentration of elemental or molecular constituents in a sample through the use of spectrometric measurements. One particular technique, spectrophotometric analysis, is a method of chemical analysis based on the absorption or attenuation of electromagnetic radiation of a specified wavelength or frequency. A spectrophotometer for providing such analysis generally consists of a source of radiation, such as a light bulb; a monochromator containing a prism or grating which disperses the light so that only a limited wavelength, or frequency range is allowed to irradiate the sample; the sample itself; and a detector, such as a photocell, which measures the amount of light transmitted by the sample.

The near ultraviolet spectral region from 200 to 400 nm is commonly used in chemical analysis. An ultraviolet spectrophotometer usually includes at least a lamp as a radiation source, a sensor and appropriate optical components. Simple inorganic ions and their complexes as well as organic molecules can be detected and determined in this spectral region.

In most quantitative analytical work, a calibration or standard curve is prepared by measuring the absorption of a known amount of a known absorbing material at the wavelength at which it strongly absorbs. The absorbance of the sample is read directly from the measuring circuit of the spectrophotometer.

Most gases have at least one well-defined peak of absorption at a certain wavelength. Ozone ($O_3$), for example, has one peak of absorption at 253.7 nm, in the ultraviolet range of the spectrum. The concentration of a selected gas in a sample can be obtained by solving an equation, known as the Beer-Lambert equation as follows:

$$I_s = I_r * e^{-\epsilon L C}$$

Where:
$I_s$ is the intensity of light from the sample;
$I_r$ is the intensity of light from the reference;
$\epsilon$ is the ozone absorption coefficient constant at the wavelength used;
L is the length of the absorption chamber (path length of the light); and
C is the concentration of gas in weight/volume.

Since L and $\epsilon$ are fixed quantities, gas concentration can be determined by measuring the intensities $I_s$ and $I_r$. The Beer-Lambert equation provides an absolute determination of gas concentration. The relationship requires the measurement of a "reference" light intensity and a "sample" light intensity.

Most gas analyzers currently employed for process gas measurement, are fed with gas from a small gas sidestream; and it is the gas from the sidestream that is analyzed. However, the diversion of gas can be wastefull. For example, with respect to ozone generators a portion ozone output from the generator is diverted to the analyzer and subsequently directed to a scrubber or gas neutralization/ destruction device. It would be desirable to eliminate such a diversion and to directly sample much of or the entirety of the generator output. This would increase the effective output of the generator and eliminate the requirement for a scrubber. However, known ultraviolet analyzers are functionally limited to very small test cells that are unable to accommodate significant flow volumes.

An additional problem with respect to known light absorption analyzers is that in order to measure the concentration of a given gas, the analyzer requires a "zero gas present" reference, or a zero reference, to compare with the gas stream. One approach for providing a zero reference involves using a beam splitter to divert light away from an absorption cell and an associated sensor for measurement by a second sensor. However, as the optical components exposed to the gas stream are gradually soiled to varying degrees during usage and the optical components associated with the diverted light are not soiled, a drift between the two measurements develops which becomes progressively more inaccurate over time.

SUMMARY OF THE INVENTION

The present invention provides a gas detection and measurement system that can in many cases allow the entire fluid output of certain gas generators to flow through the system while analyzing the fluid to determine the concentration of a selected gas within the fluid. The gas detection and measurement system includes a light source, a light sensor array, a test cell having a first fluid port and a second fluid port, and first and second optical paths from the light source to the light sensor through the test cell. The first and second optical paths have different lengths. As fluid flows through the test cell, light intensity measurements are taken along the first and second optical paths so that the concentration of a target gas within the fluid can be calculated. The system minimizes drift problems associated with soiled optical elements and reduces the frequency of required "zeroing" or calibration procedures.

In an exemplary embodiment, the first optical path is defined by a first pair of spaced-apart optical elements and the second optical path is defined by a second pair of spaced-apart optical elements. In another embodiment of the invention, the first and second optical paths are defined by a first optical element that is movable with respect to a second optical element.

DESCRIPTION OF THE DRAWINGS

Other features and benefits of the invention can be more clearly understood with reference to the specification and the accompanying drawing in which.

DETAILED DESCRIPTION OF THE INVENTION

Figure 1:
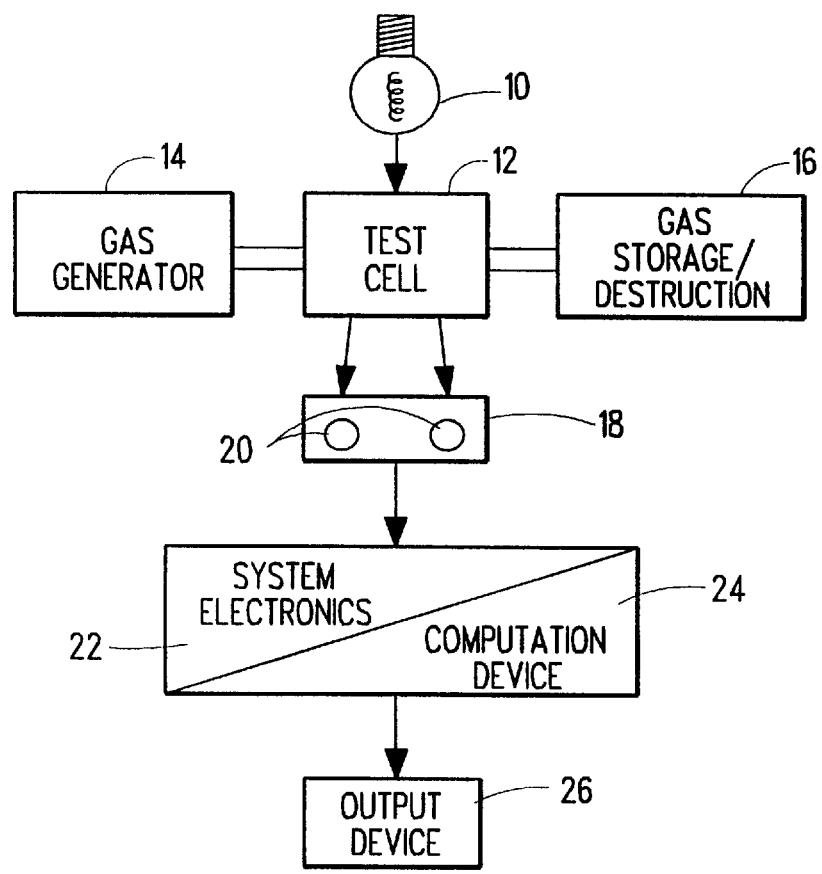
FIG. 1 is a schematic drawing of a gas detection and measurement system in accordance with the invention.

FIG. 1 is a drawing of a gas detection and measurement system in accordance with the invention. The system includes a light source 10 capable of emitting light in a selected spectral range as required for spectrochemical analysis of gas, as is known to those skilled in the art. In the exemplary embodiment the light source 10 emits ultraviolet light useful for analyzing a fluid that includes ozone.

The system further includes a test cell 12 that receives light from the light source 10 and allows light to exit therefrom. Either a gas or a liquid, hereinafter collectively referred to as a fluid, is directable from a first location 14, such as a gas source or generator, through the test cell 12 to a second location 16, such as a reactor or a gas storage or destruction device. The test cell 12 includes or defines at least one absorption chamber or cuvette that provides a first light path having a length $L_1$ and a second light path having a length $L_2$ for light passing through the test cell 12. Particular values for $L_1$ and $L_2$ depend on the output of the light source 10, the wavelength employed, sensor sensitivity, and the resolution capability of the system electronics.

A sensor array 18, including one or more sensors 20, is exposed to the light, if any, that exits the test cell 12 after passing therethrough. When the sensors are on a shared substrate, sensor drift is minimized. The sensor array 18 provides an output indicative of first path light intensity $I_{s1}$ and an output indicative of second path light intensity $I_{s2}$ to system electronics 22 that include a computation device 24 for performing required calculations. User defined output based upon the measurements and calculations is presented on an output device 26 such as a plotter, a printer, or a video display.

After obtaining measurements of first and second path light intensity, it is possible to determine gas concentration by applying the rewritten Beer-Lambert equation as follows:

$$C = \frac{\ln \frac{I_{s2} I_{r1}}{I_{s1} I_{r2}}}{\epsilon(L_1 - L_2)}$$

where:
$I_{r1}$ is the intensity of light through a reference gas along a first path;
$I_{r2}$ is the intensity of light through a reference gas along a second path;
$I_{s1}$ is the intensity of light from a gas sample being evaluated along the first path;
$I_{s2}$ is the intensity of light from a gas sample being evaluated along the second path;
$L_1$ is the first path length;
$L_2$ is the second path length;
ln is a natural logarithm function;
$\epsilon$ is the ozone absorption coefficient constant at the wavelength used; and
C is the concentration of gas in weight/volume.

Figure 2:
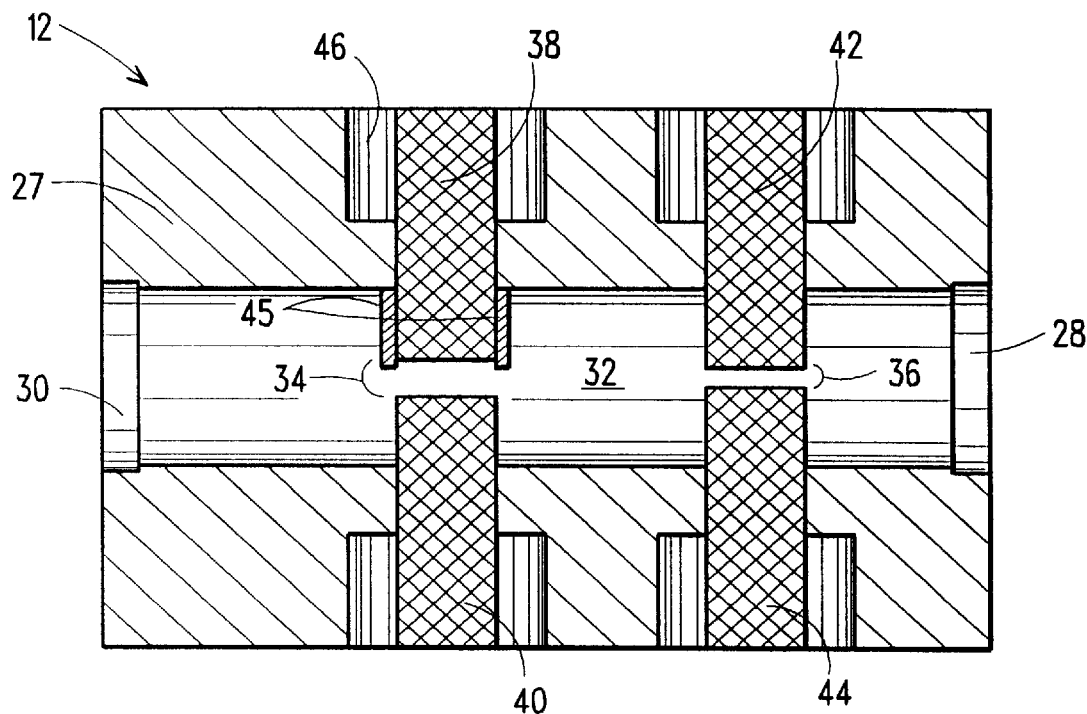
FIG. 2 is a sectional view of a test cell for the system illustrated in FIG. 1.
Figure 3:
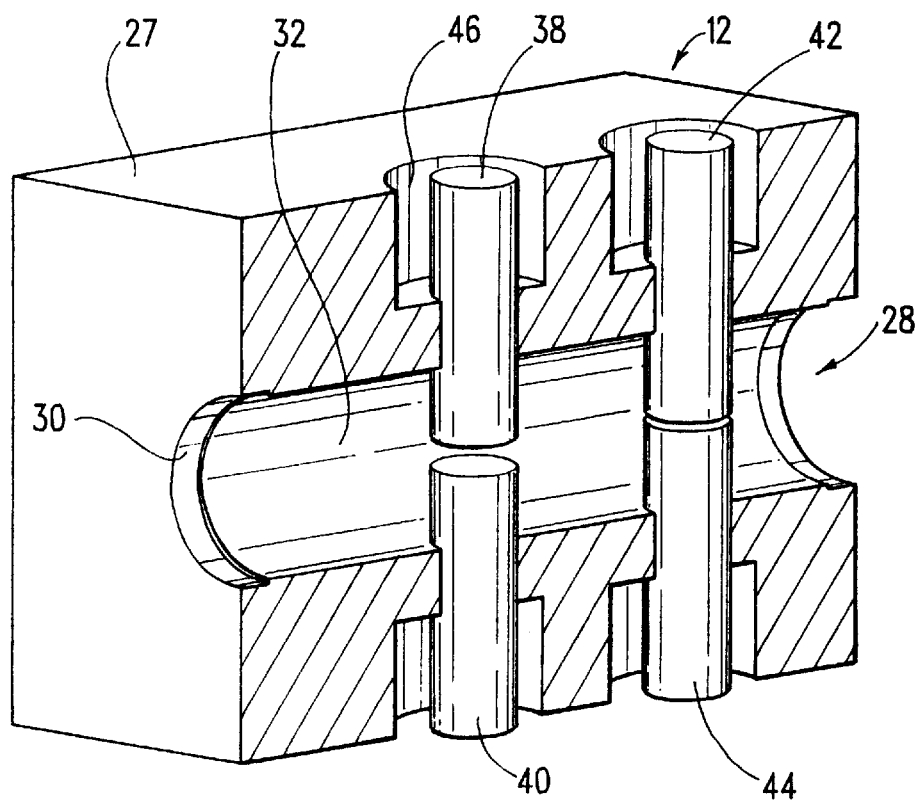
FIG. 3 is a cutaway perspective view of the test cell shown in FIG. 2.

FIGS. 2–5 illustrate exemplary embodiments of the test cell 12 that are configured to provide first and second light paths of unequal lengths. Referring now to FIGS. 2 and 3 collectively, the exemplary test cell 12 includes a test cell body 27 that defines a first port 28 and a second port 30. The ports can be configured to mate with fluid couplings in a manner known to those skilled in the art so that the first port 28 is in fluid communication with the gas generator 14 and the second port is in fluid communication with the gas storage device 16. The region between the ports is a cuvette or absorption cell 32 which defines a fluid flow path for fluid passing through the absorption cell from the first port 28 to the second port 30 or from the second port to the first port.

First and second optical paths, 34 and 36 respectively, are provided which allow light from the light source 10 to pass through the test cell 12, the fluid passing through the absorption cell 32, and to exit from the absorption cell and the test cell. In this embodiment, a first optical element 38 is aligned with and opposes a second optical element 40. Similarly, a third optical element 42 is aligned with and opposes a fourth optical element 44. The first optical path 34 is defined by the gap between the first optical element 38 and the second optical element 40. The second optical path is defined by the gap between the third optical element 42 and the fourth optical element 44. It should be noted that the gaps are of different widths and that they define the first and second path lengths for use in the above rewritten Beer-Lambert equation. The selection of the particular path lengths is a function of the wavelength of light provided by the light source 10, the spectral absorption characteristics of the fluid, and by the concentration of the gas to be measured. Typically, the gaps or path lengths are not larger than the diameter of the absorption cell 32. Additionally, although two optical path lengths are shown, another embodiment of the invention that is not illustrated includes a third optical path, having no gap, which provides additional zero-reference data.

In the illustrated embodiment, the optical elements 38, 40, 42, and 44 are optical quality rods that protrude through apertures in a metal or plastic test cell body 27 and into the absorption cell 32 at an angle of approximately 90° degrees with respect to the fluid flow path. However, in other embodiments the optical elements are not perpendicular to the fluid flow path and can even be can be parallel to the fluid flow path. The specific angle of orientation of the optical elements, which may lie in the range of 0° to 90° degrees with respect to the fluid flow path, is determined by particular optical element geometry, size, and desired flow characteristics within the absorption cell 32.

It has been discovered that a configuration that causes fluid to pass through the absorption cell 32 in a turbulent manner tends to cause the optical elements to soil in a substantially uniform fashion. Turbulence can be induced by extending the optical elements into the fluid flow path. It should be understood that even though the fluid flow is turbulent, the fluid still moves along a predetermined flow path. Although selected embodiments of the invention call for turbulent flow, the invention is also operable with non-turbulent or laminar flow through the absorption cell 32.

An additional consideration with respect to the optical elements is the prevention of cross-talk between the pairs of elements. Therefore, to prevent light from passing from the first optical element 38 into the fourth optical element 44 or from the third optical element 42 into the second optical element 40, the pairs of elements are spaced apart a distance that is determined by the diameter of optical elements, the path lengths, the fluid medium, and the light source. Another approach for preventing cross-talk is to provide one or more of the optical elements with shielding 45.

The optical elements can be fabricated from known optical lens materials such as fused silica. Additionally, although the optical elements illustrated herein have circular cross-sections, geometries such as square, oval, and others are also suitable. Metals and plastics suitable for fabricating the test cell body 27 include stainless steel, aluminum, Peek, Vespel, Teflon and polyethylene. The particular material selection is determined by the specific application.

The first optical element 38 and the third optical element 42 are positioned to receive light directly from the light source 10 or indirectly through light guides (not shown) such as optical fibers. The second optical element 40 and the fourth optical element 44 are directly aligned with the sensor(s) 20 of the sensor array 18. Alternatively, light can be conducted from the second and fourth optical elements, 40 and 44, respectively, to the sensor(s) 20 of the sensor array 18 using light guides (not shown). The test cell 12 is shown with recesses 46 associated with each of the optical elements, wherein the recesses and optical elements are adapted for mating with light guides. Additionally, the recesses 46 are configured to allow a sealant, such as an O-ring, to be positioned therein to prevent gas from escaping from the test cell body 27.

The test cell described with respect to FIGS. 2 and 3 is capable of being dimensioned to permit the full fluid output of the gas generator 14 to pass through the absorption cell 32. In an exemplary application the fluid is a gaseous mixture of oxygen and ozone having a maximum flow rate of 15 liters per minute. The absorption cell 32 is approximately 0.250 inches in diameter, the optical elements 38, 40, 42, and 44 are 0.125 inches in diameter, the first optical path 34 is 0.040 inches in length, and the second optical path 36 is 0.010 inches in length. The optical elements are unshielded and the pairs of optical elements are spaced 0.250 inches apart.

Figure 4:
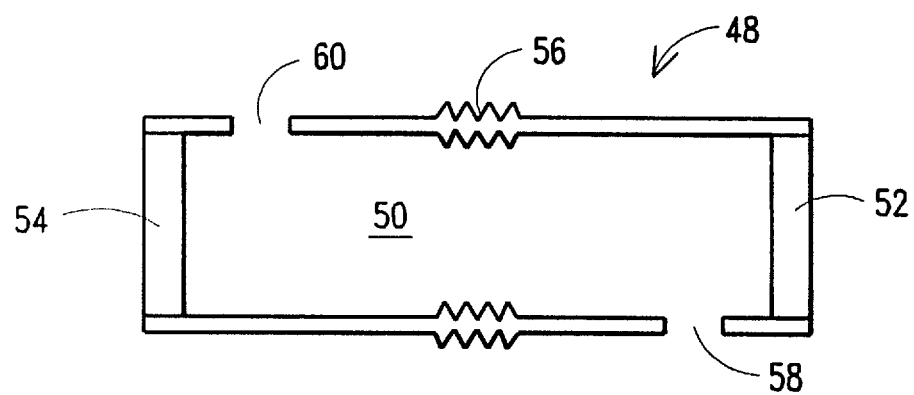
FIG. 4 is a schematic illustration of an alternative embodiment of the test cell.
Figure 5:
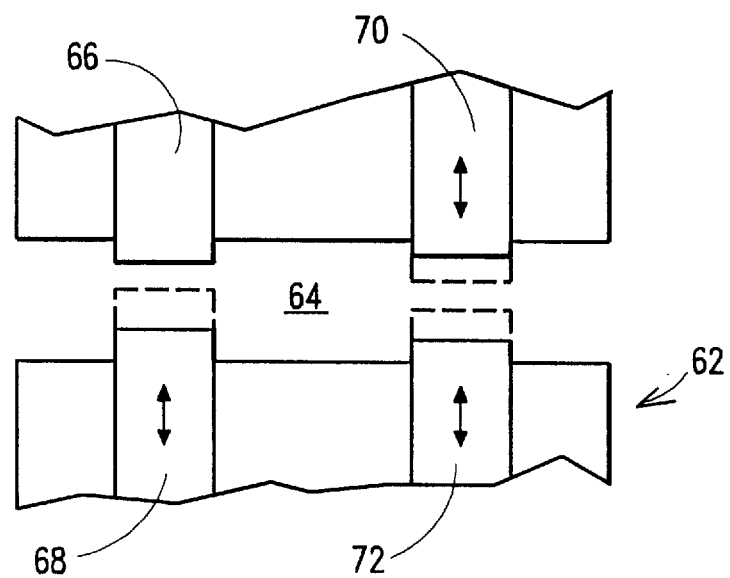
FIG. 5 is a schematic illustration of yet another embodiment of the test cell.

In another embodiment, a test cell having variable geometry features provides more than one optical path length, wherein a first measurement is made at $L_1$ and a second measurement is made at $L_2$. Embodiments of such a device are illustrated in FIGS. 4 and 5, wherein optical elements are movable with respect to each other. With respect to each of the variable geometry embodiments, it should be noted that the provision of a single pair of optical elements for making first and second path length measurements requires only a single sensor. Additionally, because the same pair of optical elements is used to make first and second path length measurements, any potential problem associated with differential soiling of optical element pairs is eliminated in certain situations.

Referring now to FIG. 4, a test cell 48 is shown which comprises a single absorption cell 50, and a first optical element 52 that is movable with respect to an opposing second optical element 54 to lengthen or shorten the distance or path length between the optical elements. In this embodiment the absorption cell 50 includes a variable geometry wall portion 56, such as bellows or a resilient material, that permits the length of the absorption cell to be changed. The material selected for the wall portion 56 is determined by the movement required and the specific application. In an embodiment of the test cell adapted for measuring high concentrations of ozone with ultraviolet light, the difference between $L_1$ and $L_2$ is about 1 mm. A displacement of this magnitude can be achieved by providing a wall portion 56 fabricated from speaker diaphragm material. Turbulent fluid flow can provided within the absorption cell 50 by offsetting a first port 58 from a second port 60 or by providing turbulence generators.

Referring now to FIG. 5, a test cell 62 includes an absorption cell 64 defined by fixed length walls includes a first optical element 66 and a second optical element 68, wherein one or both of the optical elements are movable from a first position to a second position to provide first and second path lengths. Although this embodiment is directed to a single pair of optical elements, a variable geometry embodiment can include a second pair of optical elements 70 and 72 that are movable from a first position to a second position.

With respect to the embodiments of FIGS. 4 and 5, movement of the walls or of the optical elements is effected using mechanical and/or electromechanical devices known to those skilled in the art. For example, the rods can be slid back and forth through apertures in a test cell body by electromechanical servos.

Although the invention has been shown and described with respect to exemplary embodiments thereof, various other changes, omission and additions in form and detail thereof may be made therein without departing from the spirit and scope of the invention.

What is claimed is:

1. A gas detection and measurement system comprising:
   a light source;
   a light sensor;
   a test cell having a first port and a second port;
   a first optical path defined by a first pair of spaced-apart optical elements from said light source to said light sensor through said test cell, said first optical path defining a first path length;
   a second optical path defined by a second pair of spaced-apart optical elements from said light source to said light sensor through said test cell, said second optical path defining a second path length, wherein said first path length is different than said second path length, and
   system electronics for determining the light intensity through a fluid to be measured alone said first optical path and the light intensity of said fluid along said second optical path, and for comparing said light intensities along said first and second optical paths against the light intensities along said first and second optical paths of a reference fluid so as to determine the concentration of a component of said fluid to be measured.

2. The system of claim 1 wherein said system electronics further comprise a computation device for determining the concentration of a component of said fluid to be measured flowing through said test cell by applying the following equation:

$$C = \frac{\ln \frac{I_{s2} I_{r1}}{I_{s1} I_{r2}}}{\epsilon(L_1 - L_2)}$$

where: $<I_{r1}$ is the light intensity through said reference fluid along said first optical path;
$I_{r2}$ is the light intensity through said reference fluid along said second optical path;
$I_{s1}$ is the light intensity from said fluid to be measured along said first optical path;
$I_{s2}$ is the light intensity from said fluid to be measured along said second optical path;
$L_1$ is said first optical path length;
$L_2$ is said second optical path length;
ln is a natural logarithm function;
$\epsilon$ is the fluid component absorption coefficient constant at the wavelength used; and
C is the concentration of said fluid component in weight/volume.

3. The system of claim 1, wherein said test cell includes an absorption cell which defines a fluid flow path from said first port to said second port.

4. The system of claim 3, wherein a portion of said first pair of spaced-apart optical elements and a portion of said second pair of spaced-apart optical elements are within said absorption cell.

5. The system of claim 4, wherein said portion of said first pair of spaced-apart optical elements and said portion of said second pair of space-apart optical elements are disposed within said absorption cell at a range of angles between 0 and 90 degrees with respect to said fluid flow path.

6. The system of claim 5, wherein said first pair of spaced-apart optical elements and said second pair of spaced-apart optical elements include opposing optical rods disposed within said absorption cell at approximately 90 degrees with respect to said fluid flow path.

7. The system of claim 5, wherein at least one of said first pair of spaced-apart optical elements and said second pair of spaced-apart optical elements are shielded to prevent cross-talk.

8. The system of claim 5, wherein said first pair of spaced-apart optical elements and said second pair of spaced-apart optical elements are separated by a distance sufficient to prevent cross-talk.

9. The system of claim 8 wherein said system electronics further comprise a computation device for determining the concentration of a component of a fluid flowing through said test cell by applying the following equation:

$$C = \frac{\ln \frac{I_{s2} I_{r1}}{I_{s1} I_{r2}}}{\epsilon (L_1 - L_2)}$$

where:

$I_{r1}$ is the light intensity through said reference fluid along said first optical path;

$I_{r2}$ is the light intensity through said reference fluid along said second optical path;

$I_{s1}$ is the light intensity from said fluid to be measured along said first optical path;

$I_{s2}$ is the light intensity from said fluid to be measured along said second optical path;

$L_1$ is said first optical path length;

$L_2$ is said second optical path length;

ln is a natural logarithm function;

$\epsilon$ is the fluid component absorption coefficient constant at the wavelength used; and C is the concentration of said fluid component in weight/volume.

10. The system of claim 1, wherein said first optical path and said second optical path are defined by a first optical element that is movable with respect to a second optical element.

11. The system of claim 10, wherein said first optical element is slidably disposed within said test cell and is movable from a first position to a second position.

12. The system of claim 10, wherein said first optical element and said second optical element are moveable with respect to each other by changing the length of said test cell.

13. The system of claim 12, wherein said test cell includes a variable geometry wall portion.

14. The system of claim 13, wherein said variable geometry wall portion includes resilient material.

15. The system of claim 13, wherein said variable geometry wall portion includes bellows.

* * * * *